United States Patent
Taniguchi et al.

(10) Patent No.: US 8,148,289 B2
(45) Date of Patent: Apr. 3, 2012

(54) TITANIUM OXIDE PHOTOCATALYST AND METHOD FOR PRODUCING THE SAME

(75) Inventors: Noboru Taniguchi, Osaka (JP); Shuzo Tokumitsu, Hyogo (JP); Tomohiro Kuroha, Osaka (JP); Kenichi Tokuhiro, Osaka (JP); Akio Nakashima, Osaka (JP); Keita Kobayashi, Osaka (JP); Shinji Nakahara, Osaka (JP)

(73) Assignees: Panasonic Corporation, Osaka (JP); Sakai Chemical Industry Co., Ltd., Osaka (JP)

( * ) Notice: Subject to any disclaimer, the term of this patent is extended or adjusted under 35 U.S.C. 154(b) by 47 days.

(21) Appl. No.: 12/596,293

(22) PCT Filed: Apr. 18, 2008

(86) PCT No.: PCT/JP2008/001022
§ 371 (c)(1),
(2), (4) Date: Oct. 16, 2009

(87) PCT Pub. No.: WO2008/132824
PCT Pub. Date: Nov. 6, 2008

(65) Prior Publication Data
US 2010/0111817 A1 May 6, 2010

(30) Foreign Application Priority Data

Apr. 18, 2007 (JP) .................................. 2007-109796
Oct. 1, 2007 (JP) .................................. 2007-257917

(51) Int. Cl.
*B01J 27/06* (2006.01)
*B01J 23/00* (2006.01)
*C01G 23/047* (2006.01)

(52) U.S. Cl. .......................... 502/224; 502/350; 423/610
(58) Field of Classification Search .................. 502/224, 502/350; 423/610
See application file for complete search history.

(56) References Cited

U.S. PATENT DOCUMENTS

| 5,759,948 | A | 6/1998 | Takaoka et al. |
| 6,281,277 | B1 * | 8/2001 | Ishii et al. ..................... 524/444 |
| 7,521,391 | B2 * | 4/2009 | Sakatani et al. ............. 502/239 |

(Continued)

FOREIGN PATENT DOCUMENTS

JP 1-218635 8/1989

(Continued)

OTHER PUBLICATIONS

"Preparation of anatase powders from fluorine-complexed titanium(iv) aqueous solution using microwave irradiation," Jose A. Ayllon et al. Journal of Materials Chemistry, vol. 10 (2000), pp. 1911-1914.*

(Continued)

*Primary Examiner* — Patricia L Hailey
(74) *Attorney, Agent, or Firm* — Hamre, Shumann, Mueller & Larson, P.C.

(57) ABSTRACT

A titanium oxide photocatalyst that is capable of improving a decomposition rate, and a method for producing the same are provided. The titanium oxide photocatalyst of the present invention is a titanium oxide photocatalyst containing at least an anatase-type titanium oxide and fluorine, wherein a content of the fluorine is 2.5 wt % to 3.5 wt %, and 90 wt % or more of the fluorine is chemically bonded to the anatase-type titanium oxide.

8 Claims, 2 Drawing Sheets

U.S. PATENT DOCUMENTS

| | | | |
|---|---|---|---|
| 7,521,394 B2 * | 4/2009 | Xie et al. | 502/350 |
| 7,771,688 B2 * | 8/2010 | Lee et al. | 423/386 |
| 2005/0020440 A1 | 1/2005 | Domen et al. | |
| 2006/0210798 A1 * | 9/2006 | Burda | 428/402 |

FOREIGN PATENT DOCUMENTS

| | | |
|---|---|---|
| JP | 7-303835 | 11/1995 |
| JP | 11-188703 | 7/1999 |
| JP | 11-319570 | 11/1999 |
| JP | 2000-107610 | 4/2000 |
| JP | 2002-136811 | 5/2002 |
| JP | 2003-236389 | 8/2003 |
| JP | 2004-292225 | 10/2004 |

OTHER PUBLICATIONS

"Fluorine-doped TiO2 powders prepared by spray pyrolysis and their improved photocatalytic activity for decomposition of gas-phase acetaldehyde," Di Li et al. Journal of Fluorine Chemistry 126 (2005), pp. 69-77.*

"Synthesis of fluorine-doped titania-coated activated carbon under low temperature with high photocatalytic activity under visible light," Jingjing Xu et al. Journal of Physics and Chemistry of Solids 69 (2008), pp. 2366-2370.*

Heller, et al., "Controlled Suppression or Enhancement of the Photoactivity of Titanium Dioxide (Rutile) Pigment", Proceedings Electrochemical Society, 1988, vol. 88, No. 14, pp. 23-33.

Wang, et al., "Wide-Range Tuning of the Titanium Dioxide Flat-Band Potential by Adsorption of Fluoride and Hydrofluoric Acid", J. Phys. Chem., 1990, vol. 94, pp. 4276-4280.

Janczyk, et al., "Singlet Oxygen Photogeneration at Surface Modified Titanium Dioide", J. Am. Chem. Soc., 2006, vol. 128, No. 49, pp. 15574-15575.

* cited by examiner

TITANIUM OXIDE PHOTOCATALYST AND METHOD FOR PRODUCING THE SAME

TECHNICAL FIELD

The present invention relates to a titanium oxide photocatalyst and to a method for producing the same.

BACKGROUND ART

Recently, titanium oxide photocatalysts have been put into practical use in various situations, for the purposes of sterilization, antifouling, and the like. The use of the same now is not limited to outdoor use, but is spreading to indoor use for the purposes of sterilization, deodorization, and the like. Because of this, a titanium oxide has been demanded that can be excited efficiently even by an energy in a visible region in a titanium oxide excitation system that conventionally has required an energy in an ultraviolet region. Such demand often is met by a titanium oxide supporting a foreign element or forming a solid solution with a foreign element. A wavelength for exciting the titanium oxide can be controlled depending on the type of a foreign element to be added.

However, in many cases, such a treatment that causes titanium oxide to support a foreign element or causes titanium oxide to form a solid solution with a foreign element significantly reduces an efficiency of excitation inherent to the titanium oxide. In return for the excitability with respect to visible light, an effect to be achieved originally by ultraviolet rays is reduced, which results in a decrease in activity in many cases.

Conventionally, it is known that the photocatalytic activity of titanium oxide is enhanced by elimination of lattice defects in titanium oxide using a mineral acid or the like (Non-Patent Document 1). Especially, it is known that a hydroxyl group on a surface of titanium oxide can be replaced easily with fluorine. Therefore, there have been proposals to treat titanium oxide with a fluorine compound such as hydrofluoric acid so as to enhance the photocatalytic performance in the titanium oxide excitation system using ultraviolet rays (Non-Patent Document 2, Patent Documents 1 and 2). However, some types of titanium oxide treated as above did not fully exhibit the effect.

On the other hand, regarding deodorization and purification of air, a technology that is capable of promptly deodorizing and decomposing four major odorous components—acetaldehyde, acetic acid, ammonia and sulfur compound gas (e.g. hydrogen sulfide and methyl mercaptan)—has been demanded. Exemplary methods of the above technology are as follows: a method of concentrating and storing odor using an adsorbent such as activated carbon or zeolite; and a method of directly decomposing odor by thermal decomposition, thermal catalytic decomposition, ozone decomposition, plasma discharge decomposition, photocatalyst decomposition, or the like.

[Patent Document 1] JP 07-303835 A
[Patent Document 2] JP 2004-292225 A
[Non-Patent Document 1] Proceedings Electrochemical Society 1988, vol. 88, no. 14, pp. 23-33
[Non-Patent Document 2] The Journal of Physical Chemistry 1990, vol. 94, pp. 4276-4280

DISCLOSURE OF INVENTION

Problem to be Solved by the Invention

However, the method using an adsorbent only provides poor adsorbability with respect to acetaldehyde, which is highly contained in mainstream smoke and secondary smoke of tobacco products, and therefore has a problem that odor once adsorbed is again released. Moreover, the direct decomposition method using thermal decomposition or catalytic decomposition has problems in heat generation and power consumption; ozone decomposition and plasma discharge decomposition have a problem in safety because of ozone generation; and photocatalyst decomposition has a problem in the decomposition rate. Especially, in photocatalyst decomposition, as compared with the other methods, a superior ability of eliminating acetaldehyde is exhibited owing to the gas adsorbability originally possessed by titanium oxide used as a photocatalyst material, but the decomposition rate is insufficient for practical use Therefore, it is an object of the present invention to provide a titanium oxide photocatalyst that is capable of improving a decomposition rate, and a method for producing the same

Means for Solving Problem

A titanium oxide photocatalyst of the present invention includes at least an anatase-type titanium oxide and fluorine, wherein a content of the fluorine is 2.5 wt % to 3.5 wt %, and 90 wt % or more of the fluorine is bonded chemically to the anatase-type titanium oxide.

A method of the present invention for producing a titanium oxide photocatalyst is a method for producing a titanium oxide photocatalyst containing at least an anatase-type titanium oxide and fluorine, and includes the steps of mixing a fluorine compound and an aqueous dispersion solution of an anatase-type titanium oxide that adsorbs n-butylamine in an amount of 8 μmol/g or less, and when a pH of the mixed solution exceeds 3, adjusting the pH at 3 or less with an acid, whereby the titanium oxide and the fluorine compound are reacted with each other in the mixed solution; and washing a reaction product obtained by the reaction, whereby a titanium oxide photocatalyst is obtained that contains at least the anatase-type titanium oxide and the fluorine, wherein a content of the fluorine is 2.5 wt % to 3.5 wt %, and of an entirety of the fluorine, a proportion of fluorine chemically bonded to the anatase-type titanium oxide is 90 wt % or more.

Further, a method of the present invention for producing a titanium oxide photocatalyst is a method for producing a titanium oxide photocatalyst containing at least an anatase-type titanium oxide and fluorine, and includes the steps of adjusting a pH of an aqueous dispersion solution of a titanium oxide with an alkaline solution until the pH thereof becomes in a range of 7.5 to 9.5, and thereafter filtering the solution; re-dispersing a filtration residue obtained by the filtration into water; obtaining a suspension by adding a fluorine compound to the re-dispersion solution obtained by the re-dispersion, and thereafter adjusting a pH of the suspension with an acid until the pH thereof becomes 3 or less, whereby the titanium oxide and the fluorine compound are reacted with each other; and washing a reaction product obtained by the reaction, whereby a titanium oxide photocatalyst is obtained that contains at least the anatase-type titanium oxide and the fluorine, wherein a content of the fluorine is 2.5 wt % to 3.5 wt %, and of an entirety of the fluorine, a proportion of the fluorine chemically bonded to the anatase-type titanium oxide is 90 wt % or more.

Effects of the Invention

A titanium oxide photocatalyst and a method for producing the same according to the present invention can provide a titanium oxide photocatalyst having high photocatalytic activity. Further, the titanium oxide photocatalyst according to the present invention can improve, for example, an odorous component decomposition rate.

Figure 1:
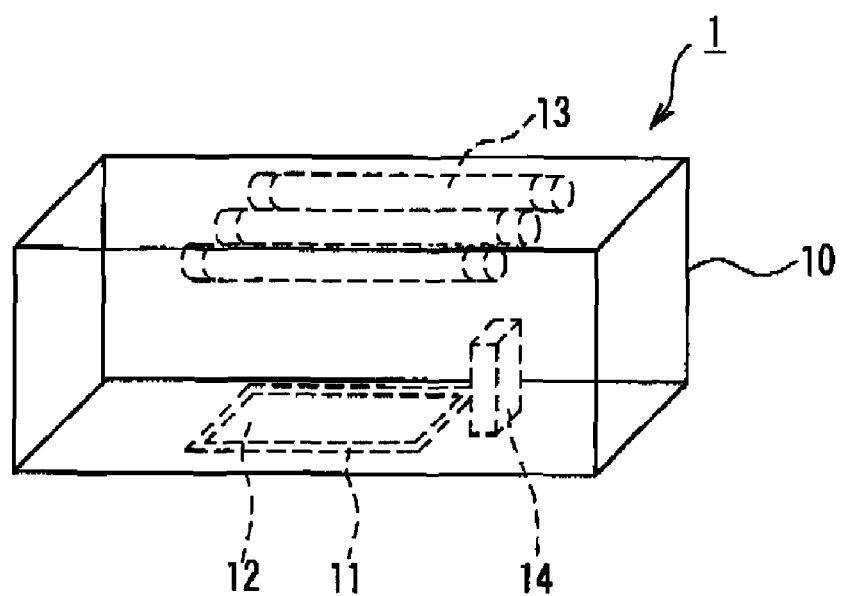
FIG. 1 is a perspective view of an air purification module using a titanium oxide photocatalyst of the present invention.

EXPLANATION OF REFERENCE CODES 1 air purification module
2 liquid purification module
10 container
11 substrate
12 titanium oxide photocatalyst
13, 23 black light
14 blowing fan
20 magnetic stirrer
21 petri dish
22 stirrer bar
24 stand

DESCRIPTION OF PREFERRED EMBODIMENTS

A titanium oxide photocatalyst of the present invention is a titanium oxide photocatalyst that contains at least an anatase-type titanium oxide (hereinafter also referred to as "titanium oxide" simply) and fluorine, wherein a content of the fluorine is 2.5 wt % to 3.5 wt %, and 90 wt % or more of the fluorine is chemically bonded to the above anatase-type titanium oxide. This makes it possible to improve the photocatalytic activity, whereby, for example, an odorous component decomposition rate can be improved.

In the present invention, a photocatalyst refers to a substance that shows catalytic activity when irradiated with light such as ultraviolet rays, and preferably, to a substance that, when irradiated with light, can decompose and eliminate various organic and inorganic compounds and perform sterilization. The titanium oxide photocatalyst of the present invention preferably can be used for, for example, decomposing and eliminating odorous components such as acetaldehyde and methyl mercaptans; sterilizing and eliminating fungi and algae; oxidatively decomposing and eliminating nitrogen oxides; and imparting an anti-fouling function by causing glass to have ultra-hydrophilic properties.

In the present invention, examples of the photocatalytic activity include a function of decomposing organic compounds oxidatively when the titanium oxide photocatalyst is irradiated with ultraviolet rays. The photocatalytic activity of the present invention can be evaluated by, for example, a carbon dioxide generation rate that indicate a rate at which carbon dioxide is generated along with the oxidation of organic compounds when the organic compounds in a gaseous or liquid state and the titanium oxide photocatalyst coexist and are irradiated with ultraviolet rays of 400 nm or less. Preferably, the photocatalytic activity can be evaluated by, for example, a carbon dioxide generation rate at which carbon dioxide is generated by the oxidative decomposition of acetaldehyde. The reaction is expressed by a reaction formula (1) shown below.

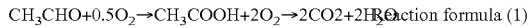

$$CH_3CHO + 0.5O_2 \rightarrow CH_3COOH + 2O_2 \rightarrow 2CO_2 + 2H_2O \quad \text{Reaction formula (1)}$$

The titanium oxide photocatalyst of the present invention contains fluorine in the range of 2.5 wt % to 3.5 wt % in element content; more preferably, in the range of 2.7 wt % to 3.3 wt %; and further preferably, in the range of 2.9 wt % to 3.1 wt %. Setting the content of fluorine to 2.5 wt % or more makes it possible to improve the photocatalytic activity, while setting the content of fluorine to 3.5 wt % or less makes it possible to suppress a decline in the photocatalytic activity.

The reason why the titanium oxide photocatalyst of the present invention improves the photocatalytic activity is uncertain, but it is assumed as follows: by setting the content of fluorine at 2.5 wt % or more, the fluorine, which has a large electronegativity, comes to stay on a surface of the titanium oxide. Owing to the electron-withdrawing function of the fluorine located on the surface of the titanium oxide, for example, a hydroxyl group located adjacent thereto is activated, whereby a hydroxyl radical tends to be generated. As a result, the photocatalytic reaction can be accelerated. Although the photocatalytic reaction can develop even when the content of fluorine is 2.5 wt % or less, the effect of accelerating the photocatalytic reaction can be enhanced greatly when the content of fluorine is 2.5 wt % or more.

Further, the reason why the titanium oxide photocatalyst of the present invention can suppress a decline in the photocatalytic activity is uncertain, yet it is assumed as follows: by setting the content of fluorine at 3.5 wt % or less, for example, the amount of fluorine covering the surface of the titanium oxide can be kept in an adequate range, whereby the number of hydroxyl groups required for the photocatalytic reaction can be ensured.

Furthermore, in the titanium oxide photocatalyst of the present invention, 90 wt % or more of fluorine is chemically bonded to the titanium oxide. This allows the fluorine to exhibit its own electron-withdrawing function effectively, whereby the photocatalytic reaction accelerating effect can be enhanced. Specifically, the above chemical bond preferably is an ionic bond because in such a case fluorine and titanium oxide are bonded to each other firmly and the photocatalytic reaction accelerating effect is enhanced further. It should be noted that the ionic bond of fluorine and titanium oxide can be determined by a measurement using a photoelectron spectroscopic analyzer, which is described later.

In the titanium oxide photocatalyst of the present invention, from the viewpoint of accelerating the photocatalytic reaction, a proportion of fluorine chemically bonded to the titanium oxide is 90 wt % or more of an entirety of the fluorine in the titanium oxide photocatalyst preferably 95 wt % or more; and more preferably 100 wt %, that is, the entirety of the fluorine contained in the titanium oxide photocatalyst is chemically bonded to the titanium oxide. In the titanium oxide photocatalyst of the present invention, the content of fluorine chemically bonded to titanium oxide is, for example, 2.35 wt % to 3.5 wt %; preferably 2.5 wt % to 3.5 wt %; and more preferably 2.5 wt % to 3.3 wt %.

In the present invention, a chemical bond between titanium oxide and fluorine refers to a state in which titanium oxide and fluorine are chemically bonded to each other, and preferably, to a state in which titanium oxide and fluorine are, not supported or mixed, but bonded to each other at the atomic level. In the present invention, chemically-bonded fluorine refers to, of the fluorine contained in the titanium oxide photocatalyst, the fluorine that is not eluted into water, for example. The amount of such fluorine chemically bonded to the titanium oxide can be measured by the following method: first, a titanium oxide photocatalyst is dispersed into water; then the dispersion solution is kept at pH=3 or less, or pH=10 or more with a pH adjuster (e.g. hydrochloric add, ammonia water); the amount of fluorine ion eluted into water is measured by a colorimetric titration, or the like; and the above eluted amount is subtracted from the total amount of the fluorine contained in the titanium oxide photocatalyst. Thus, the amount of the fluorine chemically bonded to the titanium oxide can be determined. The amount of fluorine ion eluted into water can be measured as in Examples described later.

In the titanium oxide photocatalyst of the present invention, it is preferable that at least a part of the fluorine chemically bonded to the titanium oxide is located on surfaces of titanium oxide. Because the photocatalytic reaction mainly occurs on surfaces of titanium oxide, if the fluorine is located on surfaces of titanium oxide, the photocatalytic reaction accelerating effect is enhanced further. It should be noted that the amount of fluorine chemically bonded to the titanium oxide on surfaces of the titanium oxide can be determined in a measurement using a photoelectron spectroscopic analyzer, as in Examples described later.

In the present specification, "titanium oxide and fluorine are bonded ionically" refers to a case in which, when the titanium oxide photocatalyst is analyzed by a photoelectron spectroscopic analyze; the catalyst shows a spectrum such that a peak-top of 1s orbital of fluorine ($F_{1s}$) appears in a range from 683 eV to 686 eV. This is ascribed to titanium fluoride, which results from ionic bonding of fluorine and titanium, having a peak-top value falling in the above range.

In the case where the titanium oxide photocatalyst of the present invention includes sodium, and where a content of sodium in the entirety of the titanium oxide photocatalyst is assumed to be A wt % and a content of fluorine in the entirety of the titanium oxide photocatalyst is assumed to be B wt %, a ratio A/B is preferably 0.01 or less; more preferably 0.005 or less; and further preferably 0.001 or less. If the ratio A/B is 0.01 or less, a decline in the photocatalytic activity can be suppressed. The reason is uncertain, yet it is assumed that, for example, a decrease in the amount of sodium with respect to fluorine causes the decline in the photocatalytic activity due to the reaction between sodium and fluorine to be suppressed. It should be noted that it is most preferable that the content of sodium is 0, that is, it is most preferable that the ratio A/B is 1. Regarding impurities other than sodium also, it is preferable that there are less impurities; and it is most preferable that there are no impurities. Examples of an element that can be impurities include potassium, aluminum, and transition metals.

Regarding the titanium oxide photocatalyst of the present invention, a specific surface area thereof is preferably in a range of 200 $m^2/g$ to 350 $m^2/g$; and more preferably, in a range of 250 $m^2/g$ to 350 $m^2/g$. Here, in the present invention, the specific surface area refers to a value of a surface area per 1 g of the titanium oxide photocatalyst in powder form measured by a BET method (nitrogen adsorption-description method). When the specific surface area is 200 $m^2/g$ or more, the area in contact with an object to be decomposed can be large. Further, in the case where an anatase-type titanium oxide is used, and if the specific surface area thereof is 350 $m^2/g$ or less, a photocatalytic reaction with higher efficiency can be achieved compared to the case where an amorphous titanium oxide is used. Here, the anatase-type titanium oxide refers to a titanium oxide showing a diffraction peak at a diffraction angle 2θ=25.5 degrees in a measurement with a powder X-ray diffractometer using copper electrodes as working electrodes.

Next, a method for producing a titanium oxide photocatalyst according to the present invention is described. It should be noted that the producing method described below is a preferable method for producing the above-described titanium oxide photocatalyst of the present invention. Therefore, descriptions of the same contents as above are omitted herein.

The method for producing a titanium oxide photocatalyst according to the present invention is a method for producing a titanium oxide photocatalyst that contains at least an anatase-type titanium oxide and fluorine, and the method includes the steps of adjusting a pH of an aqueous dispersion solution of a titanium oxide with an alkaline solution until the pH thereof becomes in a range of 7.5 to 9.5, and thereafter filtering the solution; re-dispersing a filtration residue obtained by the filtration into water; obtaining a suspension by adding a fluorine compound to the re-dispersion solution obtained by the re-dispersion, and thereafter, when a pH of the suspension exceeds 3, adjusting the pH of the suspension with an acid as required until the pH thereof becomes 3 or less, whereby the titanium oxide and the fluorine compound are caused to react with each other; and washing a reaction product obtained by the reaction. With this method, the titanium oxide photocatalyst of the present invention described above can be produced easily. Therefore, the method for producing a titanium oxide photocatalyst according to the present invention preferably is a method for producing the titanium oxide photocatalyst of the present invention. With the present method, if the amount of added fluorine compound is increased, the titanium oxide dissolves itself. Therefore, the content of fluorine can be controlled easily to 3.5 wt % or lower. Further, in the case where the washing with water (water washing) is carried out in the washing step, the water washing preferably is carried out until an electric conductivity of water used in the washing becomes 1 mS/cm or less, as an index for washing. The water used for washing in the present invention refers to, for example, water that is used for washing a reaction product and thereafter is collected. The electric conductivity can be measured in a manner as in Examples to be described later.

In the present invention, the aforementioned re-dispersion solution contains an anatase-type titanium oxide having such a surface acidity that an amount of adsorbed n-butylamine per 1 gram of the titanium oxide is, for example, 8 μmol or less. Thus, using as a starting material the anatase-type titanium oxide having a surface that is almost basic, a titanium oxide photocatalyst can be prepared that contains fluorine in a range of 2.5 wt % to 3.5 wt % as an element. Therefore, in the foregoing producing method, the steps of "adjusting a pH of an aqueous dispersion solution of a titanium oxide with an alkaline solution until the pH thereof becomes in a range of 7.5 to 9.5, and thereafter filtering the solution" and "re-dispersing the filtration residue obtained by the filtration into water" may not be used, but instead, an aqueous dispersion solution of an anatase-type titanium oxide that adsorbs n-butylamine in an amount of 8 μmol/g or less may be used.

Therefore, the method for producing a titanium oxide photocatalyst according to the present invention is, in another aspect, a method for producing a titanium oxide photocatalyst containing at least an anatase-type titanium oxide and fluorine, and includes the steps of mixing a fluorine compound and an aqueous dispersion solution of an anatase-type titanium oxide that adsorbs n-butylamine in an amount of 8 μmol/g or less, and when a pH of the mixed solution exceeds 3, adjusting the pH at 3 or less with an acid, whereby the titanium oxide and the fluorine compound are caused to react with each other in the mixed solution: and washing a reaction product obtained by the reaction. With this method, the titanium oxide photocatalyst of the present invention can be produced. Therefore, the method for producing a titanium oxide photocatalyst according to this another aspect preferably is a method for producing the titanium oxide photocatalyst of the present invention.

As the anatase-type titanium oxide that adsorbs n-butylamine in an amount of 8 μmol/g or less, for example, SSP-25 manufactured by SAKAI Chemical Industry Co., Ltd. can be used. As the aqueous dispersion solution of the same, for example, CSB-M manufactured by SAKAI Chemical Industry Co., Ltd can be used.

Here, the method for measuring the amount of adsorbed n-butylamine per 1 gram of titanium oxide is as follows. One gram of a titanium oxide sample dried at 130° C. for 2 hours is weighed in a 50-mL stoppered Erlenmeyer flask, and 30 mL of a n-butylamine solution diluted with methanol to have a normality of 0.003 N is added the foregoing titanium oxide sample. Then, this is subjected to ultrasonic dispersion for 1 hour, and is left to stand for 10 hours. 10 mL of supernatant fluid of the same is sampled. The sampled supernatant fluid is subjected to potentiometric titration using a perchloric acid solution diluted with methanol to have a normality of 0.003 N, and from the titrated amount of at the point of neutralization, the amount of adsorbed n-butylamine can be determined.

In the present invention, the anatase-type titanium oxide having such a surface acidity that an amount of adsorbed n-butylamine per 1 gram of titanium oxide is 8 μmol or less preferably contains sodium as impurities in an amount of 1000 ppm by weight (wt ppm) or less. If the content of sodium as impurities is 1000 wt ppm or less, the deterioration of photocatalytic activity can be suppressed. The reason for this is uncertain, but it is assumed that, for example, sodium reacts with fluorine, whereby the inhibition of the reaction between fluorine and titanium oxide can be prevented.

Further, as an alkaline solution used at the stage of preparation of the starting material, and as additives to be added as required after the reaction with fluorine, those which substantially do not contain sodium are desirable. Examples of the alkaline solution include ammonia water, an aqueous ammonium carbonate solution, and an aqueous hydrazine solution.

In the present invention, in the step of re-dispersing the filtration residue obtained by the filtration into water, the filtration residue preferably is in a state of not being dried when being re-dispersed into water. This is because the dispersibility of the filtration residue in the re-dispersion solution can be improved.

In the present invention, a specific method for obtaining the redispersion solution is not limited particularly. The re-dispersion solution may be prepared by, for example, any one of the methods shown below, or may be prepared by, for example, dispersing a powder-form titanium oxide available from the market (e.g., SSP-25 manufactured by SAKAI Chemical Industry Co., Ltd.) into pure water.

Method 1

An aqueous titanyl sulfate solution is heated to a temperature in a range of 80° C. to 100° C. so as to be hydrolyzed, and a slurry aqueous solution of white precipitate thus obtained is cooled. The pH of the obtained white precipitate slurry (aqueous dispersion solution of titanium oxide) is adjusted with ammonia water added to the slurry, until the pH becomes in a range of 7.5 to 9.5. Then, the shiny is filtered. The filtration residue thus obtained is washed with water thoroughly so that salts as impurities are removed. A cake made of this filtration residue thus obtained is re-dispersed in pure water, whereby a re-dispersion solution of an anatase-type titanium oxide can be obtained.

Method 2

After ammonia water is added to an aqueous titanyl sulfate solution, a pH of the obtained aqueous dispersion solution of titanium oxide is adjusted with ammonia water added to the dispersion solution until the pH becomes in a range of 7.5 to 9.5. Then, the slum is filtered. The filtration residue thus obtained is washed with water thoroughly so that salts as impurities are removed. A cake made of this filtration residue thus obtained is heated at 100° C., aged, and re-dispersed in pure water, whereby a re-dispersion solution of an anatase-type titanium oxide can be obtained.

Method 3

An aqueous titanium tetrachloride solution is heated so as to be hydrolyzed, and the pH of the obtained white precipitate slurry (aqueous dispersion solution of titanium oxide) is adjusted with ammonia water added to the slurry until the pH becomes in a range of 7.5 to 9.5. Then, the slum is filtered. The filtration residue thus obtained is washed with water thoroughly so that salts as impurities are removed. A cake made of this filtration residue thus obtained is heated to a temperature in a range of 80° C. to 100° C., aged, and re-dispersed in pure water, whereby a redispersion solution of an anatase-type titanium oxide can be obtained.

Method 4

Titanium tetraalkoxide is hydrolyzed in a solvent, and a pH of a suspension of the precipitate obtained (aqueous dispersion solution of titanium oxide) is adjusted by adding ammonia water to the suspension, until the pH becomes in a range of 7.5 to 9.5. Then, the suspension is filtered. The filtration residue thus obtained is washed with water thoroughly so that salts as impurities are removed. A cake made of this filtration residue thus obtained is heated to a temperature in a range of 80° C. to 100° C., aged, and re-dispersed in pure water, whereby a re-dispersion solution Ian anatase-type titanium oxide can be obtained.

Crystallinity of the anatase-type titanium oxide in the re-dispersion solution thus obtained preferably is such that a diffraction peak appears at a diffraction angle 2θ=25.5°, when it is measured by drying the re-dispersion solution at 50° C. under a reduced pressure so that dry powder is obtained, and measuring the crystallinity of the powder with a powder X-ray diffractometer using copper electrodes as working electrodes. This is because titanium oxide having such a characteristic is a crystallized anatase titanium oxide, and if this is used as a starting material, the photocatalytic activity can be improved.

In the present invention, the fluorine compound to be added to the re-dispersion solution is not particularly limited, but examples of the same include ammonium fluoride, potassium fluoride, sodium fluoride, and hydrofluoric acid. Among these, ammonium fluoride, potassium fluoride, and hydrofluoric acid are preferred. When a fluorine compound is added to a re-dispersion solution, it is necessary to add a fluorine compound at least so that an amount of fluorine as an element becomes 2.5 wt % or more with respect to the titanium oxide photocatalyst obtained.

Examples of the method for adding the fluorine compound include a method of adding the above-described fluorine compound in a solid state to the re-dispersion solution, a method of adding an aqueous solution of the above-described fluorine compound to the redispersion solution, and a method of bubbling fluorine gas or hydrofluoric acid gas in the redispersion solution. Among these, from the viewpoint of cost efficiency and handleability, the method of adding the solid fluorine compound to the re-dispersion solution, and the method of adding an aqueous solution of the fluorine compound to the re-dispersion solution are preferable. Further, from the viewpoint of the efficiency of reaction between titanium oxide and fluorine, it is preferable that the re-dispersion solution obtained and the fluorine compound are mixed, without a hydrothermal treatment being carried out under such conditions that a specific surface area would not decrease. Time for the treatment for the fluorine compound is not limited particularly, but is preferably in a range of 5 minutes to 90 minutes. The time more preferably is in a range of 30 minutes to 60 minutes. In the case where the time is set at 5 minutes or more, the fluorine compound added is dispersed sufficiently. In the case where the time is set at 90 minutes or less, titanium oxide having high activity can be obtained. Further, the temperature for the treatment of the fluorine compound preferably is 40° C. or lower. In the case where the temperature is set at 40° C. or lower, a decrease in the specific surface area of titanium oxide can be prevented. The temperature for the treatment of a fluorine compound normally is 10° C. or higher.

In the present invention, examples of acid used for the adjustment of a pH include hydrochloric acid, nitric acid, sulfuric acid, and hydrofluoric acid. An upper limit of the pH of a suspension obtained by adding a fluorine compound to a re-dispersion solution of titanium oxide and a mixed solution containing the anatase-type titanium oxide and a fluorine compound is 3 or less. A lower limit of the pH of the suspension and the mixed solution is not limited particularly, but from the viewpoint of cost efficiency and handleability, the pH preferably is 1 or more.

In the present invention, a reaction product obtained through the reaction step is washed with, for example, water. This makes it possible to remove fluorine that has not reacted with titanium oxide in the reaction step, unnecessary salts, dissolved impurities, and the like. Therefore, the photocatalytic activity can be improved.

In the case where the washing is carried out with water (water washing), the washing preferably is carried out until an electric conductivity of water used in the washing becomes 1 mS/cm or less, as an index for washing. In the case where the washing is carried out until an electric conductivity of water used in the washing becomes 1 mS/cm or less, unnecessary salts, dissolved impurities, etc can be removed adequately. Here, immediately after the treatment with a fluorine compound, the washing preferably is carried out with the treatment liquid with the same liquid composition, without the pH thereof being adjusted. This is because the washing with the treatment liquid with the same liquid composition makes it possible to remove impurities dissolved in the liquid easily, and hence, improves the photocatalytic activity. It should be noted that as the washing method, a method using a centrifuge, filtration equipment of any one of various types, a rotary washing machine or the like can be used, for example.

In the present invention, the titanium oxide photocatalyst obtained as described above may be subjected to a finishing treatment as required, depending on the use of the photocatalyst. For example, in the case where the photocatalyst is finished into a powder form through a drying step, it may be subjected to any conventionally known treatment for avoiding the aggregation caused by the drying, and any means for loosening aggregated powder may be used. In order to loosen powder aggregated due to the drying, any common guider may be used, but the grinding has to be carried out under such conditions that the photocatalytic activity would not deteriorate. For example, in order to prevent titanium oxide crystals from being destroyed, the grinding power has to be decreased.

Further, the titanium oxide photocatalyst having been washed through the above-described washing step may be dispersed in a solvent again so as to be used as an aqueous, oily, or emulsified dispersion solution. Here, a wet-type grinder may be used in order to loosen calcine, but a type of equipment and conditions that would not deteriorate the photocatalytic activity have to be chosen, as described above. For example, in the case of a dispersing device using a grinding medium, the concentration of titanium oxide preferably is increased in order to prevent the mixing of impurities caused by the abrasion of the medium. A diameter of the medium preferably is decreased in order to avoid the destruction of crystals of titanium oxide caused by impact of the medium.

Additionally, a surface treatment may be performed as required, depending on the use of the photocatalyst. In this case, examples of a commonly known method for this include a method of causing titanium oxide to support, on its surfaces, an adsorption component or an adsorbent such as silica, apatite, or zeolite, or contrarily, a method of causing titanium oxide to be supported by an adsorbent. In the case where a surface treatment is applied in this manner, materials used in the treatment have to be selected so that no deterioration of the photocatalytic activity should be caused or the deterioration ratio should fall in a tolerable range.

The following describes an exemplary use embodiment in which the titanium oxide photocatalyst of the present invention is used, while referring to the drawings.

Use Embodiment 1

FIG. 1 is a perspective view of an air purification module using the titanium oxide photocatalyst of the present invention. As shown in FIG. 1, an air purification module 1 includes a container 10, a substrate 11 provided on a bottom face of the container 10, a titanium oxide photocatalyst 12 formed on the substrate 11, black lights 13 disposed in the container 10 so as to face the titanium oxide photocatalyst 12, and a fan 14 for blowing odorous components in the container 10 toward the titanium oxide photocatalyst 12.

The substrate 11 is not limited particularly, and a substrate made of a metal, a resin, glass, ceramics, paper or the like may be used. The shape of the substrate is not limited to a flat shape, and any of various types such as a honeycomb form or a filter form may be selected depending on the deodorization method.

The titanium oxide photocatalyst 12 may be in a form of a layer or a film having a certain thickness. Besides, since the photocatalytic reaction occurs mainly on surfaces of the titanium oxide photocatalyst 12, the thickness of the titanium oxide photocatalyst 12 is not limited particularly, and there is substantially no thickness dependence. It should be noted that the titanium oxide photocatalyst 12 is formed on the substrate 11 by, for example, coating. In order to increase the adhesion thereof to the substrate 11, an inorganic binder may be interposed therebetween.

As the black lights 13, black lights that emit light having a wavelength of 400 nm or less may be used, for example. The black lights 13 preferably are disposed so that the titanium oxide photocatalyst 12 is irradiated uniformly with light. The light intensity is, for example, 1 mW/cm$^2$ or more, and the photocatalytic activity can be increased by an increase in the light intensity. On the other hand, from the viewpoint of the light uniformity, power consumption, and lifetime, the light intensity preferably is about 0.5 mW/cm$^2$ to 5 mW/cm$^2$.

The air purification module 1 is used in the following manner. First, odorous components are introduced into the container 10, and the odorous components are sent toward the titanium oxide photocatalyst 12 using the blowing fan 14, so that the titanium oxide photocatalyst 12 is caused to adsorb the odorous components. At the same time, the black lights 13 irradiate the titanium oxide photocatalyst 12 with light having a wavelength of 400 nm or less. In this way, the odorous components can be destroyed oxidatively.

Use Embodiment 2

Figure 2:
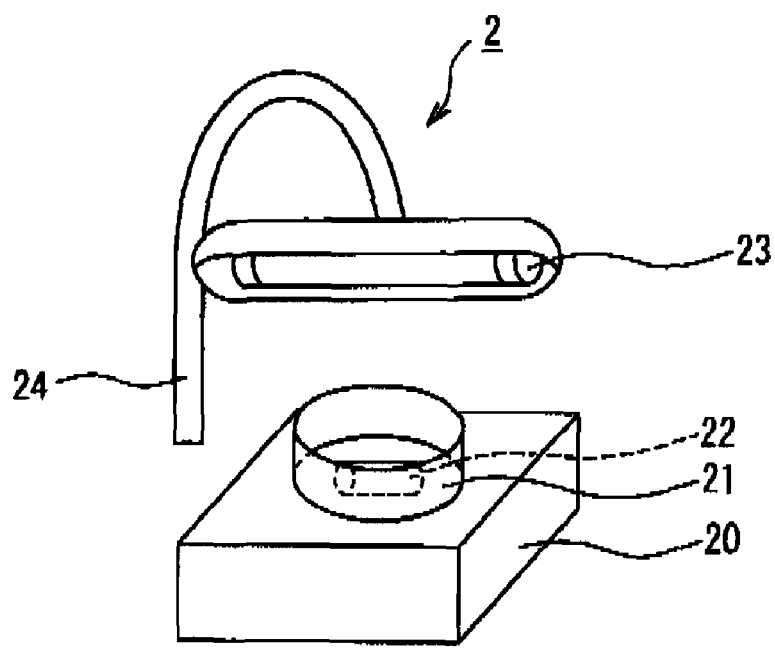
FIG. 2 is a perspective view of a liquid purification module using the titanium oxide photocatalyst of the present invention.

FIG. 2 is a perspective view of a liquid purification module using the titanium oxide photocatalyst of the present invention. As shown in FIG. 2, the liquid purification module 2 includes a magnetic stirrer 20, a Petri dish 21 disposed on the magnetic stirrer 20, a stirrer bar 22 disposed in the Petri dish 21, black light 23 disposed so as to face the Petri dish 21, and a stand 24 that holds the black light 23.

The liquid purification module 2 is used in the following manner. First, a slurry (not shown) containing the titanium oxide photocatalyst and a liquid-form organic substance is fed to the Petri dish 21, and the slurry is stirred with the stirrer bar 22 rotated by the magnetic stirrer 20. At the same time, the black light 23 irradiates the slurry with light having a wavelength of 400 nm or less. In this way, the liquid-form organic substance can be decomposed.

EXAMPLES

Hereinafter, Examples of the present invention will be described together with Comparative Examples. It should be noted that the present invention is not limited to the following Examples.

Example 1

A solution of titanyl sulfate (manufactured by SAKAI Chemical Industry Co., Ltd.) in which the concentration as to titanium oxide was 100 g/L and the concentration as to sulfuric acid was 250 g/L was kept at 100° C. for 3 hours to be hydrolyzed thermally. The pH of the obtained slurry aqueous solution was adjusted with ammonia water until the pH became 8.0, and was filtered. Then, the substance obtained by filtration was washed thoroughly with water to remove salts as impurities. Here, the water washing was performed until the electric conductivity of the washing liquid became 200 µS/cm. Pure water was added to the cake thus obtained so that the concentration of the titanium oxide therein would become 150 g/L, and was stirred, whereby a re-dispersion solution of the titanium oxide was prepared. After that, a hydrofluoric acid (manufactured by Wako Pure Chemical industries, Ltd., guaranteed reagent) equivalent to 5.0 wt % in terms of fluorine (element) with respect to titanium oxide was added to this re-dispersion solution so as to cause a reaction at 25° C. for 60 minutes while the pH thereof was kept at 3. The obtained reaction product was washed thoroughly with water to remove salts as impurities. Here, the water washing was performed until the electric conductivity of the washing liquid became 1 mS/cm or less. Then, this was dried in air at 130° C. for 5 hours so as to be powdered, whereby a titanium oxide photocatalyst of Example 1 was obtained. The titanium oxide photocatalyst of Example 1 had a specific surface area of 259 $m^2/g$ (determined by the BET method). Further, regarding the obtained titanium oxide photocatalyst, the amount of eluted fluorine was measured by a measuring method to be described later, and was found to be 5 wt %. That is, 95 wt % of fluorine in the titanium oxide photocatalyst was bonded chemically to the anatase-type titanium oxide. It should be noted that a part of the above re-dispersion solution was dried at 50° C. under a reduced pressure so as to be powdered, and the amount of n-butylamine adsorbed by the obtained powder was measured by the aforementioned measuring method. The amount was found to be 2 µmol/g.

Example 2

A titanium oxide photocatalyst of Example 2 was obtained in the same manner as in Example 1 described above, except that hydrofluoric acid (manufactured by Wako Pure Chemical Industries, Ltd., guaranteed reagent) equivalent to 7.5 wt % in terms of fluorine (element) was used as a hydrofluoric acid to be added to the re-dispersion solution. The titanium oxide photocatalyst of Example 2 had a spec iBc surface area of 251 $m^2/g$ (determined by the BET method), and the amount of eluted F thereof was 5 wt %. That is, 95 wt % of fluorine in the titanium oxide photocatalyst was bonded chemically to the anatase-type titanium oxide. It should be noted that in the preparation lithe titanium wade photocatalyst of Example 2, a part of the re-dispersion solution was dried at 50° C. under a reduced pressure so as to be powdered and the amount of n-butylamine adsorbed by the obtained powder was measured by the aforementioned measuring method. The amount was found to be 3 µmol/g.

Example 3

A titanium oxide photocatalyst of Example 3 was obtained in the same manner as in Example 1 described above, except that hydrofluoric acid (manufactured by Wako Pure Chemical Industries, Ltd., guaranteed reagent) equivalent to 10 wt % in terms of fluorine (element) was used as hydrofluoric acid to be added to the re-dispersion solution. The titanium oxide photocatalyst of Example 3 had a specific surface area of 260 $m^2/g$ (determined by the BET method), and the amount of eluted F thereof was 5 wt %. That is, 95 wt % of fluorine in the titanium oxide photocatalyst was bonded chemically to the anatase-type titanium oxide. It should be noted that in the preparation of the titanium oxide photocatalyst of Example 3, a part of the re-dispersion solution was dried at 50° C. under a reduced pressure so as to be powdered and the amount of n-butylamine adsorbed by the obtained powder was measured by the aforementioned measuring method. The amount was found to be 1 µmol/g.

Example 4

A titanium oxide photocatalyst of Example 4 was obtained in the same manner as in Example 1 described above, except that the temperature for the thermal hydrolysis of titanyl sulfate was set at 85° C. The titanium oxide photocatalyst of Example 4 had a specific surface area of 340 $m^2/g$ (determined by the BET method). It should be noted that in the preparation of the titanium oxide photocatalyst of Example 4, a part of the re-dispersion solution was dried at 50° C. under a reduced pressure so as to be powdered and the amount of n-butylamine adsorbed by the obtained powder was measured by the aforementioned measuring method. The amount was found to be 7 µmol/g.

Example 5

A titanium oxide photocatalyst of Example 5 was obtained in the same manner as in Example 1 described above, except that the re-dispersion solution prepared was held in an autoclave at 100° C. for 5 hours and thereafter hydrofluoric acid was added to the re-dispersion solution. The titanium oxide photocatalyst of Example 5 had a specific surface area of 205 $m^2/g$ (determined by the BET method). It should be noted that in the preparation of the titanium oxide photocatalyst of Example 5, a part of the re-dispersion solution after it was held at 100° C. for 5 hours was dried at 50° C. under a reduced pressure so as to be powdered and the amount of n-butylamine adsorbed by the obtained powder was measured by the aforementioned measuring method. The amount was found to be 8 µmol/g.

Example 6

A titanium oxide photocatalyst of Example 6 was obtained in the same manner as in Example 1 described above, except that ammonium fluoride (manufactured by Wako Pure Chemical Industries, Ltd., guaranteed reagent) equivalent to 5.0 wt % in terms of fluorine (element) was added in place of hydrofluoric acid and that, after the addition of ammonium fluoride, a reaction was allowed to occur with the pH being maintained at 1 using hydrochloric acid. The titanium oxide photocatalyst of Example 6 had a specific surface area of 270 $m^2/g$ (determined by the BET method). It should be noted that in the preparation of the titanium oxide photocatalyst of Example 6, a part of the re-dispersion solution was dried at 50° C. under a reduced pressure so as to be powdered and the amount of n-butylamine adsorbed by the obtained powder was measured by the aforementioned measuring method. The amount was found to be 4 µmol/g.

Example 7

A titanium oxide photocatalyst of Example 7 was obtained in the same manner as in Example 1 described above, except that sodium fluoride (manufactured by Wako Pure Chemical Industries, Ltd., guaranteed reagent) equivalent to 5.0 wt % in terms of fluorine (element) was added in place of hydrofluoric acid and that, after the addition of sodium fluoride, a reaction was allowed to occur with the pH being maintained at 1 using hydrochloric acid. The titanium oxide photocatalyst of Example 7 had a specific surface area of 268 $m^2/g$ (determined by the BET method). It should be noted that in the preparation of the titanium oxide photocatalyst of Example 7, a part of the redispersion solution was dried at 50° C. under a reduced pressure so as to be powdered and the amount of n-butylamine adsorbed by the obtained powder was measured by the aforementioned measuring method. The amount was found to be 5 µmol/g.

Example 8

A titanium oxide photocatalyst of Example 8 was obtained in the same manner as in Example 1 described above, except that sodium fluoride (manufactured by Wako Pure Chemical Industries, Ltd., guaranteed reagent) equivalent to 5.0 wt % in terms of fluorine (element) was added in place of hydrofluoric acid and that, after the addition of sodium fluoride, a reaction was allowed to occur with the pH being maintained at 3 using hydrochloric acid. The titanium oxide photocatalyst of Example 8 had a specific surface area of 272 $m^2/g$ (determined by the BET method). It should be noted that in the preparation of the titanium oxide photocatalyst of Example 8, a part of the re-dispersion solution was dried at 50° C. under a reduced pressure so as to be powdered and the amount of n-butylamine adsorbed by the obtained powder was measured by the aforementioned measuring method. The amount was found to be 5 µmol/g.

Comparative Example 1

A titanium oxide photocatalyst of Comparative Example 1 was obtained in the same manner as in Example 1 described above, except that a hydrofluoric acid (manufactured by Wako Pure Chemical Industries, Ltd., guaranteed reagent) equivalent to 4 wt % in terms of fluorine (element) was used as hydrofluoric acid to be added to the re-dispersion solution. The titanium oxide photocatalyst of Comparative Example 1 had a specific surface area of 268 $m^2/g$ (determined by the BET method). It should be noted that in the preparation of the titanium oxide photocatalyst of Comparative Example 1, a part of the redispersion solution was dried at 50° C. under a reduced pressure so as to be powdered and the amount of n-butylamine adsorbed by the obtained powder was measured by the aforementioned measuring method. The amount was found to be 6 µmol/g.

Comparative Example 2

A titanium oxide photocatalyst of Comparative Example 2 was obtained in the same manner as in Example 1 described above, except that when the substance obtained by filtration was washed with water and a cake was obtained, the water washing was performed until the electric conductivity of the washing liquid became 1 mS/cm. The titanium oxide photocatalyst of Comparative Example 2 had a specific surface area of 276 $m^2/g$ (determined by the BET method). It should be noted that in the preparation of the titanium oxide photocatalyst of Comparative Example 2, a part of the re-dispersion solution was dried at 50° C. under a reduced pressure so as to be powdered and the amount of n-butylamine adsorbed by the obtained powder was measured by the aforementioned measuring method. The amount was found to be 6

Comparative Example 3

A titanium oxide photocatalyst of Comparative Example 3 was obtained in the same manner as in Example 1 described above, except that when the pH of the obtained slurry aqueous solution was adjusted, the adjustment was carried out using sodium hydroxide, and that when the obtained reaction product was washed with water, the water washing was performed until the electric conductivity of the washing liquid became 400 µS/cm. The titanium oxide photocatalyst of Comparative Example 3 had a specific surface area of 255 $m^2/g$ (determined by the BET method). It should be noted that in the preparation of the titanium oxide photocatalyst of Comparative Example 3, a part of the re-dispersion solution was dried at 50° C. under a reduced pressure so as to be powdered and the amount of n-butylamine adsorbed by the obtained powder was measured by the aforementioned measuring method. The amount was found to be 30 emit.

Comparative Example 4

A titanium oxide photocatalyst of Comparative Example 4 was obtained in the same manner as in Example 1 described above, except that when the pH of the obtained slurry aqueous solution was adjusted, the adjustment was carried out using ammonia water until the pH became 7.0. The titanium oxide photocatalyst of Comparative Example 4 had a specific surface area of 271 $m^2/g$ (determined by the BET method). It should be noted that in the preparation of the titanium oxide photocatalyst of Comparative Example 4, a part of the re-dispersion solution was dried at 50° C. under a reduced pressure so as to be powdered and the amount of n-butylamine adsorbed by the obtained powder was measured by the aforementioned measuring method. The amount was found to be 13 µmol/g.

Comparative Example 5

After the re-dispersion solution was prepared in the same manner as in Example 1 described above, sodium fluoride (manufactured by Wako Pure Chemical Industries, Ltd., guaranteed reagent) equivalent to 5.0 wt % in terms of fluorine (element) with respect to titanium oxide was added to this re-dispersion solution, and a reaction was allowed to occur at 25° C. for 60 minutes with the pH thereof being maintained at 1. Thereafter, without the obtained reaction product being washed with water, the total amount of the dispersion solution was dried and solidified by evaporation in air at 130° C. for 10 hours so as to be powdered, whereby a titanium oxide photocatalyst of Comparative Example 5 was obtained. The titanium oxide photocatalyst of Comparative Example 5 had a specific surface area of 269 m$^2$/g (determined by the BET method), and the amount of eluted F thereof was 50 wt %. That is, the proportion of fluorine chemically bonded to the anatase-type titanium oxide was 50 wt %. It should be noted that in the preparation of the titanium oxide photocatalyst of Comparative Example 5, a part of the re-dispersion solution was dried at 50° C. under a reduced pressure so as to be powdered and the amount of n-butylamine adsorbed by the obtained powder was measured by the aforementioned measuring method. The amount was found to be 4 µmol/g.

Comparative Example 6

A titanium oxide photocatalyst of Comparative Example 6 was obtained in the same manner as in Example 1 described above, except that the redispersion solution prepared was held in an autoclave at 130° C. for 1 hour so that a hydrothermal reaction occurred, and thereafter hydrofluoric acid was added thereto. The titanium oxide photocatalyst of Comparative Example 6 had a specific surface area of 185 m$^2$/g (determined by the BET method). It should be noted that in the preparation of the titanium oxide photocatalyst of Comparative Example 6, a part of the re-dispersion solution after it was held at 130° C. for 1 hour was dried at 50° C. under a reduced pressure so as to be powdered and the amount of n-butylamine adsorbed by the obtained powder was measured by the aforementioned measuring method. The amount was found to be 5 µmol/g.

Comparative Example 7

A solution of titanyl sulfate (manufactured by SAKAI Chemical Industry Co., Ltd) in which the concentration as to titanium oxide was 100 g/L and the concentration as to sulfuric acid was 250 g/L was kept at 100° C. for 3 hours to be hydrolyzed thermally. The pH of the obtained slurry aqueous solution was adjusted with ammonia water until the pH became 8.0, and was filtered. Then, the substance obtained by filtration was washed thoroughly with water to remove salts as impurities. Here, the water washing was performed until the electric conductivity of the washing liquid became 200 µS/cm. The cake obtained was dried in air at 130° C. for 5 hours so as to be powdered, whereby a titanium oxide photocatalyst of Comparative Example 7 was obtained. The titanium oxide photocatalyst of Comparative Example 7 had a specific surface area of 274 m$^2$/g (determined by the BET method), and the amount of eluted F was found to be 0 wt %. It should be noted that in the preparation of the titanium oxide photocatalyst of Comparative Example 7, a part of the cake obtained was dried at 50° C. under a reduced pressure so as to be powdered, and the amount of n-butylamine adsorbed by the obtained powder was measured by the aforementioned measuring method. The amount was found to be 2 µmol/g.

Comparative Example 8

To 20 g of titanium hydroxide (principal component: β-titanium acid, manufactured by SAKAI Chemical Industry Co., Ltd.), 50 g of a 0.15 wt % aqueous ammonium fluoride solution was added and dried, whereby a mixture was obtained. 3.2 g of the obtained mixture was fed into an electric furnace (energy-saving temperature-rising electric furnace manufactured by MOTOYAMA, trade name: RE-2025D), and the temperature was increased from room temperature to 350° C. in air for 105 minutes. After it was maintained in this state for 1 hour so as to be calcined, it was cooled gradually, whereby 2.9 g of titanium oxide was obtained as a titanium oxide photocatalyst of Comparative Example 8. The titanium oxide photocatalyst of Comparative Example 8 had a specific surface area of 44 m$^2$/g (determined by the BET method), and the amount of eluted F thereof was 25 wt %. It should be noted that in the preparation of the titanium oxide photocatalyst of Comparative Example 8, a part of the cake obtained was hied at 50° C. under a reduced pressure so as to be powdered, and the amount of n-butylamine adsorbed by the obtained powder was measured by the aforementioned measuring method. The amount was found to be 8 µmol/g.

Analysis of Physical Properties

As to each of the titanium oxide photocatalysts of Examples 1 to 8 and Comparative Examples 1 to 8, the content of fluorine and the content of sodium were determined. The content of fluorine was analyzed by absorptiometry (JIS K0102), and the content of fluorine in the photocatalyst was determined by percentage by weight. Further, the content of sodium was analyzed by inductively coupled high-frequency plasma spectrometry (ICP spectrometry), and the content of sodium in the photocatalyst was determined by ppm by weight. Further, in the preparation of each titanium oxide photocatalyst, a part of the re-dispersion solution obtained (a part of the cake in the case of Comparative Example 7) was dried at 50° C. under a reduced pressure so as to be powdered. The content of sodium in the powder was analyzed by ICP spectrometry, and the content of sodium in the starting material was determined as ppm by weight. Further, as to each of the titanium oxide photocatalysts of Examples 1 and 2 and Comparative Examples 1, 2, 4, and 7, the ratio by weight of fluorine on surfaces of the photocatalyst with respect to titanium on the surfaces of the photocatalyst (hereinafter this ratio is referred to as "surface ratio") was determined by a method described below. The results of the same are shown in Table 1. It should be noted that, as shown in Table 1, the contents of sodium of Examples 1 to 3, 6 to 8 and Comparative Examples 1 and 5 were different even though the re-dispersion solutions thereof were prepared in the same way. As to the reason for this, it is considered that the difference was caused by variations in lots of titanyl sulfate as a raw material, and analytical errors. Further, the titanium oxide photocatalysts in Examples 1 to 8 were analyzed by a photoelectron spectroscopic analyzer, and every photocatalyst showed a spectrum in which a peak top of $F_{J}$, appeared in a range of 683 eV to 686 eV.

Determination of Crystal Form

As to each of the titanium oxide photocatalysts of Examples 1 to 8 and Comparative Examples 1 to 8, the crystal form thereof was identified with a powder X-ray diffractometer. A powder X-ray diffraction was determined using copper electrodes as working electrodes, and in every case of the titanium oxide photocatalyst of Examples 1 to 8 and Comparative Examples 1 to 8, a diffraction peak appeared at a diffraction angle 2θ=25.5°. From this, every photocatalyst was determined to be an anatase type.

Further, a part of each of the re-dispersion solutions prepared in Examples 1 to 8 and Comparative Examples 1 to 8 was dried at 50° C. under a reduced pressure so as to be powdered, and a powder X-ray diffraction thereof was measured in a manner as described above. In every case, a diffraction peak appeared at a diffraction angle 2θ=25.5°. In other words, titanium oxide contained in the re-dispersion solution prepared in Examples 1 to 8 and Comparative Examples 1 to 8 was an anatase-type titanium oxide.

Measurement of Electric Conductivity

The electric conductivity of water (25° C.) collected after washing was measured with a pH/cond meter (manufactured by HORIBA, Ltd, D-54 (trade name)).

Measurement of Amount of Eluted Fluorine 0.1 g of titanium oxide obtained in Example or Comparative Example was suspended in 100 ml of pure water, and after irradiated with ultrasonic waves for 15 minutes, it was centrifuged. The supernatant fluid obtained was subjected to colorimetric analysis using PACKTEST (registered trade name) manufactured by Kyoritsu Chemical Check Lab, Corp., and an amount of eluted fluorine ions was determined. Based on this amount of eluted fluorine, the amount of fluorine chemically bonded to titanium oxide can be determined.

Method for Measurement of Surface F Ratio

As to each of the titanium oxide photocatalyst powders, 1 g of the same was weighed, placed in a 10-mm-diameter molding die, and was pressed by stamping in a manner such that a load of 1 t/cm$^2$ was applied to each piece, so as to be formed into a 10-mm-diameter pellet. Then, this molded pellet was broken so that a small fraction having a flat surface was produced, and this fraction was fixed on a sample stage with a double-faced tape, as a sample to be subjected to photoelectron spectroscopy. This sample was left in vacuum for one day, and thereafter photoelectron spectra emitted from the 2p orbital of titanium (Ti), the is orbital of fluorine (F), and the 1s orbital of carbon (C) were measured with a photoelectron spectroscope (ESCA-850 model manufactured by Shimadzu Corporation, source of X-rays: MgKα) under the conditions of 8 kV and 30 mA. Then, with a value of the same emitted from the 1s orbital of C thus determined being compensated to be 284.8 eV, energies of the spectra determined by the measurement at the 2p orbital of Ti and the 1s orbital of F were compensated accordingly. With bonding energies of the spectrum being set to the corrected values, respectively, a value determined by the following calculation formula is assumed to be the surface F ratio:

Surface $F$ ratio$=N_F\times 19.0/(N_{Ti}\times 47.9)$ where $N_F$ represents the number of atoms of F determined from a spectral area of the is orbital of F, $N_{Ti}$ represents the number of atoms of Ti determined from a spectral area of the 2p orbital of Ti.

Evaluation of Photocatalytic Activity 1

Using the respective titanium oxide photocatalysts of Examples 1 to 8 and Comparative Examples 1 to 8, the aforementioned air purification modules shown an FIG. 1 were assembled, and the photocatalytic activities were evaluated. Acetaldehyde was used as an odorous component. The evaluation method is described below.

Evaluation Method using Air Purification Module

As to each of the respective titanium oxide photocatalyst powders, 5 g of the same was dispersed in ethanol and formed into paste, and then the paste was applied over 12 cm×10 cm glass substrate so as to have a size of 12 cm×6.4 cm (thickness: 3 μm), whereby a titanium oxide photocatalyst membrane was prepared. After the membrane was left for 1 hour at room temperature to allow most of the ethanol to vaporize, organic substances adhering to the surface of the titanium oxide photocatalyst membrane was decomposed completely by irradiation with ultraviolet rays having an intensity of 5 mW/cm$^2$ (center wavelength: 352 nm, UV lamp manufactured by Toshiba Lighting & Technology Corporation was used) for 240 minutes. The membrane was then left to stand in an airtight container (capacity: 16 L), and the container was filled with acetaldehyde so that the concentration of the acetaldehyde gas in the container was 500 mol ppm. After the membrane was left to stand for 60 minutes without UV irradiation and reached an adsorption equilibrium, a change in the concentration of the acetaldehyde in the container and an amount of generated carbon dioxide were analyzed by gas chromatography while the titanium oxide photocatalyst membrane was irradiated with ultraviolet rays having an intensity of 1 mW/cm$^2$ (center wavelength: 352 nm, UV lamp manufactured by Toshiba lighting & Technology Corporation was used). The superiorities and inferiorities of the respective titanium oxide photocatalysts were evaluated based on the carbon dioxide generation rates thus determined. The results are shown in Table 1.

TABLE 1

| | Physical property of starting material | | Physical property of titanium oxide photocatalyst | | | | | |
|---|---|---|---|---|---|---|---|---|
| | n-butylamine adsorption amount (μmol/g) | Na content (wt ppm) | F content (wt. %) | Na content (wt ppm) | Na content/ F content | Surface F ratio | Proportion of chemically-bonded fluorine (wt. %) | Carbon dioxide generation rate (mol ppm/hour) |
| Ex 1 | 2 | 802 | 2.9 | 229 | 0.0079 | 0.1 | 95 | 745 |
| Ex. 2 | 3 | 634 | 3.1 | 120 | 0.0039 | 0.13 | 95 | 772 |
| Ex 3 | 1 | 440 | 3.4 | 5 | 0.0002 | — | 95 | 818 |
| Ex 4 | 7 | 824 | 3 | 290 | 0.0097 | — | — | 650 |
| Ex 5 | 8 | 770 | 2.7 | 201 | 0.0074 | — | — | 670 |
| Ex 6 | 4 | 806 | 2.5 | 230 | 0.0092 | — | — | 693 |
| Ex 7 | 5 | 802 | 2.8 | 270 | 0.0096 | — | — | 689 |
| Ex. 8 | 5 | 815 | 2.5 | 293 | 0.0117 | — | — | 606 |
| Comp Ex. 1 | 6 | 812 | 2.3 | 200 | 0.0087 | 0.07 | — | 540 |
| Comp Ex. 2 | 6 | 1150 | 2.3 | 300 | 0.013 | 0.07 | — | 509 |
| Comp Ex. 3 | 30 | 4760 | 1.6 | 980 | 0.0613 | — | — | 520 |
| Comp Ex. 4 | 13 | 957 | 2.2 | 250 | 0.0114 | 0.07 | — | 571 |
| Comp Ex. 5 | 4 | 813 | 5 | 60000 | 1.2 | — | 50 | 300 |
| Comp Ex. 6 | 5 | 816 | 2.1 | 199 | 0.0095 | — | — | 387 |
| Comp Ex. 7 | 2 | 827 | 0 | 810 | — | 0 | 0 | 321 |
| Comp Ex. 8 | 8 | 77 | 1.5 | 9 | 0.0006 | — | 75 | 275 |

Table 1 shows that all the titanium oxide photocatalysts of Examples 1 to 8 of the present invention exhibited faster carbon dioxide generation rates (acetaldehyde decomposition rates) and superior photocatalytic activities compared to those of Comparative Examples 1 to 8. All the carbon dioxide generation rates of the titanium oxide photocatalysts of Examples 1 to 8 exceeded 600 mol ppm/hour. It should be noted that, as shown in Table 1, the n-butylamine adsorption amounts of the titanium oxide photocatalysts of Examples 1 to 3, 6 to 8 and Comparative Examples 1 and 5 were different even though the re-dispersion solutions thereof were prepared in the same way. It is considered that the difference was caused by variations in lots of titanyl sulfate as a raw material, and analytical errors.

Evaluation of Photocatalytic Activity 2

As to each of the titanium oxide photocatalysts of Examples 1 and 2 and Comparative Examples 1 and 7, the photocatalytic activity thereof was evaluated using the aforementioned fluid purification module shown in FIG. 2. Methylene blue, which is a pigment, was used as the liquid-form organic substance, and a degree of discoloration of methylene blue with time was measured. Details of the evaluation method are described below.

Evaluation Method Using Liquid Purification Module

As to each of the respective titanium oxide photocatalyst powders, 200 mg of the same and 1 mg of methylene blue were added to pure water, and a slurry in a total amount of 200 mL was obtained. This slurry, while being stirred with a stirrer bar, was irradiated with ultraviolet rays having an intensity of 1 mW/cm$^2$ (center wavelength: 352 um, UV lamp manufactured by Toshiba Lighting & Technology Corporation was used), without light entering from the outside. Then, from the start of the irradiation until 4 hours later, 5 mL of the slurry was sampled every one hour. Each sample was centrifuged using a centrifuge at 3000 rpm for 15 minutes, and a supernatant fluid was sampled. Then, the supernatant fluid thus sampled was placed in a quartz cell, and an absorbance thereof was measured using a spectrophotometer (manufactured by JASCO Corporation, V-570 model). It should be noted that since a phenomenon such that the wavelength of absorbed light shifted as the decomposition of methylene blue proceeded was observed the absorbance at the top point (peak position) of the curve was assumed to be the absorbance of the sample. Then, an absorbance of an aqueous methylene blue solution prepared at a different concentration preliminarily (standard fluid) was measured so that a calibration curve was produced, and a concentration (mg/L) of the methylene blue remaining in the slurry was determined based on the foregoing calibration curve and the absorbance of the supernatant fluid measured by the aforementioned method. The results are shown in Table 2 and FIG. 3. The rate of discoloration of methylene blue shown in Table 2 is calculated by the following formula:

TABLE 2

$$\text{Discoloration rate} = \frac{\text{Concentration of methylene blue (after 1-hour irradiation)}}{\text{Concentration of methylene blue (before irradiation)}}$$

| | Methylene blue discoloration rate (ppm/hour) |
|---|---|
| Ex. 1 | 4.0 |
| Ex. 2 | 4.1 |
| Comp. Ex. 1 | 2.4 |
| Comp. Ex. 7 | 2.1 |

Figure 3:
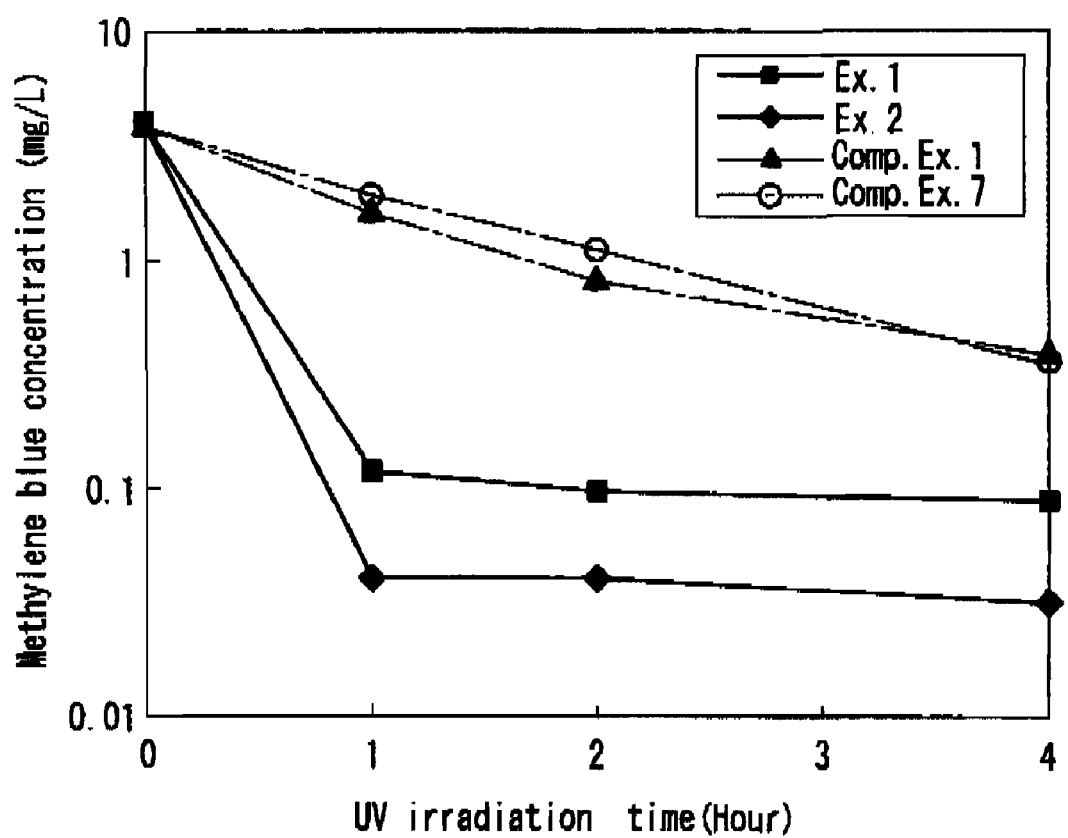
FIG. 3 is a graph showing a relationship between the ultraviolet irradiation time and the concentration of methylene blue in each of liquid purification modules of Examples of the present invention and Comparative Examples.

As is clear from Table 2 and FIG. 3, in the cases of the titanium oxide photocatalysts of Example 1 and 2 of the present invention, significantly higher rates of discoloration (decomposition of methylene blue) were observed, as compared with the cases of Comparative Examples 1 and 7, which means that the titanium oxide photocatalysts of Example 1 and 2 exhibited excellent photocatalytic activity. The discoloration rates in the cases of the titanium oxide photocatalysts of Examples 1 and 2 were about double of the discoloration rates in the cases of the titanium oxide photocatalysts of Comparative Examples 1 and 7. Further, whereas the titanium oxide photocatalysts of Comparative Examples 1 and 7 were capable of decomposing methylene blue only to a concentration of about 1 mg/L even after 4-hour UV irradiation, the titanium oxide photocatalysts of Examples 1 and 2 were capable of decomposing methylene blue to a concentration of 0.1 mg/L or less, i.e., one tenth or less of those in the cases of Comparative Examples, after about 1-hour UV irradiation.

Industrial Applicability

The present invention is useful for a purification device used for the purpose of, for example, deodorization, odor elimination, and air purification.

The invention claimed is:

1. A method for producing a titanium oxide photocatalyst containing at least an anatase-type titanium oxide and fluorine, the method comprising the steps of:
    mixing a fluorine compound and an aqueous dispersion solution of an anatase-type titanium oxide that absorbs n-butylamine in an amount of 8 μmol/g or less, and when a pH of the mixed solution exceeds 3, adjusting the pH at 3 or less with an acid, whereby the titanium oxide and the fluorine compound are caused to react with each other in the mixed solution; and
    washing a reaction product obtained by the reaction, whereby a titanium oxide photocatalyst is obtained that contains at least the anatase-type titanium oxide and the fluorine, wherein a content of the fluorine is 2.5 wt % to 3.5 wt %, and, of an entirety of the fluorine, a proportion of fluorine chemically bonded to the anatase-type titanium oxide is 90 wt % or more.

2. The method for producing a titanium oxide photocatalyst according to claim 1, wherein the content of sodium in the anatase-type titanium oxide in the aqueous dispersion solution is 1000 wt ppm or less.

3. The method for producing a titanium oxide photocatalyst according to claim 2,
    wherein the washing step is a step of washing the reaction product with water and
    the reaction product is washed until an electric conductivity of water collected after the washing becomes 1 mS/cm or less.

4. The method for producing a titanium oxide photocatalyst according to claim 1,
    wherein the washing step is a step of washing the reaction product with water and
    the reaction product is washed until an electric conductivity of water collected after the washing becomes 1 mS/cm or less.

5. A method for producing a titanium oxide photocatalyst containing at least an anatase-type titanium oxide and fluorine, the method comprising the steps of:
    adjusting a pH of an aqueous dispersion solution of a titanium oxide with an alkaline solution until the pH thereof becomes in a range of 7.5 to 9.5, and thereafter filtering the solution;
    re-dispersing a filtration residue obtained by the filtration into water;
    obtaining a suspension by adding a fluorine compound to the re-dispersion solution obtained by the re-dispersion, and thereafter adjusting a pH of the suspension with an acid until the pH thereof becomes 3 or less, whereby the titanium oxide and the fluorine compound are caused to react with each other; and washing a reaction product obtained by the reaction, whereby a titanium oxide photocatalyst is obtained that contains at least the anatase-type titanium oxide and the fluorine, wherein a content of the fluorine is 2.5 wt % to 3.5 wt %, and, of an entirety of the fluorine, a proportion of the fluorine chemically bonded to the anatase-type titanium oxide is 90 wt % or more.

6. The method for producing a titanium oxide photocatalyst according to claim 5, wherein the alkaline solution contains at least one selected from the group consisting of ammonia water, an aqueous ammonium carbonate solution, and an aqueous hydrazine solution.

7. The method for producing a titanium oxide photocatalyst according to claim 6,
wherein the washing step is a step of washing the reaction product with water and
the reaction product is washed until an electric conductivity of water collected after the washing becomes 1 mS/cm or less.

8. The method for producing a titanium oxide photocatalyst according to claim 5,
wherein the washing step is a step of washing the reaction product with water and
the reaction product is washed until an electric conductivity of water collected after the washing becomes 1 mS/cm or less.

\* \* \* \* \*